United States Patent
Xue et al.

(10) Patent No.: US 11,408,016 B2
(45) Date of Patent: Aug. 9, 2022

(54) AMINO ACID DEHYDROGENASE MUTANT AND APPLICATION IN SYNTHESIS OF L-GLUFOSINATE-AMMONIUM THEREOF

(71) Applicant: ZHEJIANG UNIVERSITY OF TECHNOLOGY, Zhejiang (CN)

(72) Inventors: Yaping Xue, Zhejiang (CN); Feng Cheng, Zhejiang (CN); Heng Li, Zhejiang (CN); Yuguo Zheng, Zhejiang (CN); Jianmiao Xu, Zhejiang (CN)

(73) Assignee: ZHEJIANG UNIVERSITY OF TECHNOLOGY, Zhejiang (CN)

( * ) Notice: Subject to any disclaimer, the term of this patent is extended or adjusted under 35 U.S.C. 154(b) by 152 days.

(21) Appl. No.: 16/978,345

(22) PCT Filed: Jun. 28, 2019

(86) PCT No.: PCT/CN2019/093453
§ 371 (c)(1),
(2) Date: Sep. 4, 2020

(87) PCT Pub. No.: WO2020/133989
PCT Pub. Date: Jul. 2, 2020

(65) Prior Publication Data
US 2021/0071215 A1      Mar. 11, 2021

(30) Foreign Application Priority Data
Dec. 28, 2018 (CN) .......................... 201811621667.8

(51) Int. Cl.
*C12P 13/04* (2006.01)
*C12N 9/06* (2006.01)

(52) U.S. Cl.
CPC ............ *C12P 13/04* (2013.01); *C12N 9/0014* (2013.01)

(58) Field of Classification Search
None
See application file for complete search history.

(56) References Cited

FOREIGN PATENT DOCUMENTS

| CN | 106978453 A | 7/2017 |
|---|---|---|
| CN | 108588045 A | 9/2018 |
| CN | 108795893 A | 11/2018 |
| CN | 109022381 A | 12/2018 |
| CN | 109609474 A | 4/2019 |
| WO | WO-02/36742 A2 | 5/2002 |
| WO | WO-2006/015885 A1 | 2/2006 |
| WO | WO-2016/001362 A1 | 1/2016 |

OTHER PUBLICATIONS

Genbank accession No. WP_060477601 (publicly available since Jan. 27, 2016, retrieved from the Internet <<https://www.ncbi.nlm.nih.gov/protein/WP_060477601.1?report=genbank&log$=protalign&blast_rank=1&RID=319YETHA013>>, retrieved on Mar. 15, 2022).*

NCBI., "NADP-Specific Glutamate Dehydrogenase [Pseudomonas monteilii]", WP_060477601.1, Genbank, Aug. 4, 2017, p. 1, sections Locus to Origin, NCBI Reference Sequence: WP_060477601.1 (XP-055722854).

Yin, Xinjian., et al., "Efficient Reductive Amination Process for Enantioselective Synthesis of L-Phosphinothricin Applying Engineered Glutamate Dehydrogenase", Applied Microbiology and Biotechnology, Springer Berlin Heidelberg, Berlin/Heidelberg, vol. 102, Issue No. 10, Mar. 16, 2019, pp. 4425-4433 (XP-036493130).

* cited by examiner

*Primary Examiner* — Suzanne M Noakes
*Assistant Examiner* — Jae W Lee
(74) *Attorney, Agent, or Firm* — Muncy, Geissler, Olds & Lowe, P.C.

(57) ABSTRACT

The present invention discloses an amino acid dehydrogenase mutant and application thereof in synthesizing L-glufosinate-ammonium, the amino acid dehydrogenase mutant is obtained by a single mutation or a multi-site mutation of the amino acid at position 95, 108, 172, 303 of the amino acid sequence shown in SEQ ID No. 2. The amino acid dehydrogenase mutant DyGDH-F95I-A108T-R172P-R303H prepared by the present invention has a specific enzyme activity that is 33 times higher than that of the original Aldo-keto reductase, and the concentration of the largest substrate, 2-carbonyl-4-(hydroxymethylphosphinyl)-butyric acid reaches 500 mM, the amino acid dehydrogenase mutant has more industrial application prospects. Using the amino acid dehydrogenase mutant to produce L-glufosinate-ammonium, the reaction time is significantly shortened, the general process takes 20 hours, and the reaction time of the present invention only requires 120 minutes, which shows that the amino acid dehydrogenase mutant has a good industrial application prospect.

7 Claims, 3 Drawing Sheets
Specification includes a Sequence Listing.

AMINO ACID DEHYDROGENASE MUTANT AND APPLICATION IN SYNTHESIS OF L-GLUFOSINATE-AMMONIUM THEREOF

The instant application contains a Sequence Listing which has been submitted in ASCII format via EFS-Web and is hereby incorporated by reference in its entirety. Said ASCII copy, created on Mar. 9, 2022 is named 2022-03-10-Sequence-Listing.txt and is 12,249 bytes in size.

TECHNICAL FIELD

The present invention relates to construction of amino acid dehydrogenase (DyGDH) mutant and develops applications of recombinant strain containing the amino acid dehydrogenase mutant and the enzyme in chiral biosynthesis of 2-amino-4-(hydroxymethylphosphinyl)-L-butyric acid ammonium (commonly known as L-glufosinate-ammonium).

BACKGROUND ART

Glufosinate-ammonium is the second largest transgenic crop-tolerant herbicide in the world, developed and produced by Hearst Corporation (now merged with Bayer), is a phosphonic acid herbicide, a glutamine synthetase inhibitor and a non-selective (killing) contact poisoning herbicide.

The activity of glufosinate-ammonium is between glyphosate and paraquat, which has the advantages of high activity, low toxicity and easy degradation, and environmental friendliness; in addition, it can also be used to screen anti-glufosinate-ammonium transgenic crops, so it is widely used, generally favored by the market and will have broad market prospects in the future.

Glufosinate-ammonium is made by mixing a pair of optical isomers, which can be resolved into laevo isomer (cis configuration D) and dextroisomer (trans configuration L), wherein only L-glufosinate-ammonium has insecticidal activity, is easily decomposed in soil, and has little damage to the environment.

The superfamily of amino acid dehydrogenases is a class of NAD(P)H-dependent oxidoreductases. The members of the family are mostly multi-subunit polymers. The molecular weight of a single subunit varies from 40 KDa to 120 KDa, and every subunit has two domains (a substrate binding domain and a coenzyme binding domain). The substrate spectrum of amino acid dehydrogenases is generally narrow, and most of the catalysates are in L-configuration.

We cloned the amino acid dehydrogenase gene from *Pseudomonas monteilii* WP_060477601.1, and realized heterologous overexpression of the gene in *Escherichia coli*, which can catalyze the asymmetric reductive amination of 2-carbonyl-4-(hydroxymethylphosphinyl)-butyric acid to L-glufosinate-ammonium, but the activity of this enzyme on 2-carbonyl-4-(hydroxymethylphosphinyl)-butyric acid was not high enough, which limited its industrial application. Based on the reported crystal structure of the amino acid dehydrogenase, molecular simulations were used to determine the spatial structure of the enzyme and possible amino acid sites related to the activity, and site-directed mutagenesis technique was used to improve the catalytic activity of the amino acid dehydrogenase on 2-carbonyl-4-(hydroxymethylphosphinyl)-butyric acid, so the enzyme will have stronger industrial application value.

SUMMARY OF THE INVENTION

Aiming at the problems that the existing amino acid dehydrogenases showed low activity and low substrate concentration on the asymmetric reductive amination of 2-carbonyl-4-(hydroxymethylphosphinyl)-butyric acid, the present invention provides an amino acid dehydrogenase mutant, and a gene recombinant strain of the amino acid dehydrogenase mutant and crude enzyme liquid thereof are used as a biocatalyst of chiral biosynthesis of L-glufosinate-ammonium and lead to improved activity of the catalyst and improved substrate concentration.

Technical solutions adopted in the present invention are as follows:

The present invention provides an amino acid dehydrogenase mutant, which is obtained by a single mutation or a multi-site mutation of the amino acid at position 95, 108, 172, 303 of the amino acid sequence shown in SEQ ID No. 2. The amino acid sequence of the original amino acid dehydrogenase DyGDH is shown in SEQ ID No. 2, and its nucleotide sequence is shown in SEQ ID No. 1.

Further, the amino acid dehydrogenase mutant is preferably obtained by: (1) mutating phenylalanine at position 95 of the amino acid sequence shown in SEQ ID No. 2 into leucine (DyGDH-F95L) or isoleucine (DyGDH-F95I); (2) mutating phenylalanine at position 95 of the amino acid sequence shown in SEQ ID No. 2 into leucine, and alanine at position 108 into threonine (DyGDH-F95L-A108T), serine (DyGDH-F95L-A108S) or tyrosine (DyGDH-F95L-A108Y); (3) mutating phenylalanine at position 95 of the amino acid sequence shown in SEQ ID No. 2 into isoleucine, and arginine at position 172 into proline (DyGDH-F95I-R172P) or valine (DyGDH-F95I-R172V); (4) mutating phenylalanine at position 95 of the amino acid sequence shown in SEQ ID No. 2 into isoleucine, alanine at position 108 into threonine, and arginine at position 172 into proline (DyGDH-F95I-A108T-R172P) or valine (DyGDH-F95I-A108T-R172V); (5) mutating phenylalanine at position 95 of the amino acid sequence shown in SEQ ID No. 2 into isoleucine, alanine at position 108 into tyrosine, and arginine at position 172 into proline (DyGDH-F95I-A108Y-R172P); or (6) mutating phenylalanine at position 95 of the amino acid sequence shown in SEQ ID No. 2 into isoleucine, alanine at position 108 into threonine, arginine at position 172 into proline and arginine at position 303 into histidine (DyGDH-F95I-A108T-R172P-R303H).

More further, the amino acid dehydrogenase mutant is preferably obtained by mutating phenylalanine at position 95 of the amino acid sequence shown in SEQ ID No. 2 into isoleucine, alanine at position 108 into threonine, arginine at position 172 into proline and arginine at position 303 into histidine (DyGDH-F95I-A108T-R172P-R303H).

The present invention also provides an encoding gene, a recombinant vector and an engineered strain of the amino acid dehydrogenase mutant. The recombinant expression vector is preferably pETDEut; the host cells are preferably *E. coli* BL21(DE3), and induced expression of the protein and cell disruption are carried out to obtain crude enzyme liquid, whose catalytic characteristic is superior to its original amino acid dehydrogenase.

The present invention also provides an application of the encoding gene of the amino acid dehydrogenase mutant in preparation of an amino acid dehydrogenase, and the application is carried out as follows: a recombinant vector containing the gene of the amino acid dehydrogenase mutant is constructed and is transformed into a host strain (preferably *E. coli*), the obtained recombinant genetically engineered strain is subjected to inducing culture to obtain culture liquid, and the culture liquid is isolated to obtain cells containing the recombinant amino acid dehydrogenase which is more catalytically active than the wild-type amino acid dehydrogenase.

The invention also provides an application of the amino acid dehydrogenase mutant in the asymmetric reductive amination of 2-carbonyl-4-(hydroxymethylphosphinyl)-butyric acid to L-glufosinate-ammonium, and the application method is specifically carried out as follows: the wet cells obtained by induction of the recombinant genetically engineered strain containing the gene of the amino acid dehydrogenase mutant and wet cells obtained by induction of an engineered strain containing the gene of the glucose dehydrogenase are mixed and resuspended in a pH7.4, 100 mM phosphate buffer, the resulting mixture is subjected to ultrasonication and centrifugation, then the resulting supernatant is used as catalyst, 2-carbonyl-4-(hydroxymethylphosphinyl)-butyric acid is used as substrate and glucose is used as auxiliary substrate, the reaction is carried out under the conditions of 35° C. and 400-600 rpm, after the reaction is completed, the reaction solution is separated and purified to obtain L-glufosinate-ammonium; the nucleotide sequence of the glucose dehydrogenase gene is shown in SEQ ID No. 3 (the amino acid sequence of the encoded protein is shown in SEQ ID No. 4).

Further, in the reaction system, the final concentration of 2-carbonyl-4-(hydroxymethylphosphinyl)-butyric acid is 300-500 mM (preferably 500 mM), the final concentration of glucose is 450-750 mM (preferably 750 mM), the amount of the catalyst is 50-100 g/L (preferably 75-80 g/L) calculated by the total amount of the wet cells before ultrasonication, the wet cells obtained by induction of the recombinant genetically engineered strain containing the gene of the amino acid dehydrogenase mutant and the wet cells obtained by induction of the engineered strain containing the gene of the glucose dehydrogenase are mixed at the mass ratio of 3:1.

Further, the wet cells containing the amino acid dehydrogenase mutant are prepared by a method as follows: the recombinant genetically engineered strain containing the gene of the amino acid dehydrogenase mutant is inoculated into LB liquid medium containing 50 μg/mL (final concentration) ampicillin, cultured at 37° C. for 8 hours, the resulting inoculum is inoculated with 2% incubating volume to fresh LB liquid medium containing 50 μg/mL (final concentration) ampicillin, cultured at 37° C. and 180 rpm for 1.5 h, then added with IPTG at a final concentration of 0.1 mM, cultured at 18° C. for 20 h, and centrifuged at 4° C. and 8000 rpm for 10 min, thereby obtaining the wet cells containing the amino acid dehydrogenase mutant.

Further, the wet cells containing the glucose dehydrogenase are prepared by the following method: the engineered strain containing the gene of the glucose dehydrogenase is inoculated into LB liquid medium containing 50 μg/mL (final concentration) kanamycin, cultured at 37° C. for 9 hours, the resulting inoculum is inoculated with 2% incubating volume to fresh LB liquid medium containing 50 μg/mL (final concentration) kanamycin, cultured at 37° C. and 180 rpm for 1.5 h, then added with IPTG at a final concentration of 0.1 mM, cultured at 28° C. for 10 h, and centrifuged at 4° C. and 8000 rpm for 10 min, thereby obtaining the wet cells containing the glucose dehydrogenase.

Further, the ultrasonication is carried out as follows: the wet cells obtained by induction of the recombinant genetically engineered strain containing the gene of the amino acid dehydrogenase mutant and the wet cells obtained by induction of engineered strain containing the gene of the glucose dehydrogenase are mixed and resuspended in the pH7.4, 100 mM phosphate buffer, the resulting mixture is subjected to ultrasonication for 15 min, and the conditions of the ultrasonication are 400 W, 1 second on, and 5 seconds off.

In the present invention, the original amino acid dehydrogenase DyGDH and the amino acid dehydrogenase mutant are both 1341 bp in total length, from the first base to the 1341th base, the start codon is ATG, and the stop codon is TAA.

The amino acid dehydrogenase mutant of the present invention is obtained by using site-directed saturation mutagenesis, which is used to mutate the gene of the amino acid dehydrogenase shown in SEQ ID No. 2, and the obtained mutant plasmid is transformed into E. coli BL21 (DE3) competent cells by heat shock, the obtained strain is subjected to inoculation, transformation, induction and cell recovery, the crude enzyme liquid is used to catalyze the preparation of L-glufosinate-ammonium from 2-carbonyl-4-(hydroxymethylphosphinyl)-butyric acid, and the specific method is carried out as follows: in the first step, the original bacteria are activated to obtain the original E. coli BL21 (DE3) pETDEut-dygdh, and the plasmid template pETDEut-dygdh is extracted and stored for use. In the second step, by comparing with DyGDH through NCBI, the PDB number of the template protein of homology modeling is obtained, the template protein crystal structure is searched in the PDB database, Modeller 9.20 is used to carry out homology modeling and molecular docking, appropriate mutation sites are selected, and the selected sites are mainly amino acid residues near the catalytic site and near the substrate-binding pocket, after designing mutation primers, pETDEut-dygdh is used as a template plasmid, mutation PCR is performed to obtain mutant plasmids, which are transformed and screened for superior mutants, and the superior mutants are subjected to sequence detection and storage.

In the present invention, the medium for the inoculation, transformation, induction and cell recovery of the genetically engineered strains containing the gene of the amino acid dehydrogenase mutant and the gene of the glucose dehydrogenase may be any medium in the art that can grow the bacteria and produce the products in the present invention, preferably LB culture medium, whose components are as follows: peptone 10 g/L, yeast powder 5 g/L, NaCl 10 g/L, dissolved in distilled water, pH 7.0. There are no special restrictions on the cultivation method and cultivation conditions, the cultivation method and conditions can be appropriately selected on the basis of factors such as different types of host and cultivation methods according to the general knowledge in the art. The glucose dehydrogenase is derived from *Exiguobacterium sibiricum*, the sequence number of the glucose dehydrogenase gene is GenBank: No. KM817194.1, the vector pET-28b (+) is used, and the recombinant expression vector pET-28b (+)-esgdh is constructed.

Compared with prior art, advantages of the present invention are mainly embodied in:

1. The amino acid dehydrogenase mutant DyGDH-F95I-A108T-R172P-R303H prepared by the present invention has a specific enzyme activity that is 33 times higher than that of the original Aldo-keto reductase, and the concentration of the largest substrate, 2-carbonyl-4-(hydroxymethylphosphinyl)-butyric acid reaches 500 mM, the amino acid dehydrogenase mutant has more industrial application prospects.

2. Using the amino acid dehydrogenase mutant to produce L-glufosinate-ammonium, the reaction time is significantly shortened, the general process takes 20 hours, and the reaction time of the present invention only requires 120 minutes, which shows that the amino acid dehydrogenase mutant has a good industrial application prospect.

SPECIFIC EMBODIMENTS

The present invention is further illustrated below with specific examples.

Example 1: Construction and Screening of the Amino Acid Dehydrogenase Mutant Library The gene of the amino acid dehydrogenase cloned from *Pseudomonas monteilii* WP_060477601.1 (the nucleotide sequence is shown in SEQ ID No. 1, and the amino acid sequence is shown in SEQ ID No. 2) was used to construct the expression vector pETDEut-dygdh, then the obtained vector was transformed into *E. coli* to obtain the original strain *E. coli* BL21(DE3)/pETDEut-dygdh.

The amino acid dehydrogenase mutant library was prepared by 4 rounds of site-directed saturation mutagenesis. The primer design was shown in Table 1. In the first round, with the vector pETDEut-dygdh as a template and F95F and F95R in Table 1 as primers, saturation mutation PCR was performed to mutate phenylalanine at position 95 of the amino acid sequence of the amino acid dehydrogenase shown in SEQ ID No. 2 into other 19 amino acids, the PCR product was transformed and spread, and the superior strain was then selected, thereby obtaining the amino acid dehydrogenase mutant pDyGDH-F95L. In the second round, with mutant pDyGDH-F95L as a template and A108F and A108R as primers, saturation mutation PCR was carried out, the PCR product was subjected to transformation and spreading, and the superior strain was selected, thereby obtaining the amino acid dehydrogenase mutant pDyGDH-F95L-A108T. In the third round, with mutant pDyGDH-F95L-A108T as a template and R172F and R172R as primers, saturation mutation PCR was carried out, the PCR product was subjected to transformation and spreading, and the superior strain was selected, thereby obtaining the amino acid dehydrogenase mutant pDyGDH-F95L-A108T-R172P. In the fourth round, with mutant pDyGDH-F95L-A108T-R172P as a template and R303F and R303R as primers, saturation mutation PCR was carried out, the PCR product was subjected to transformation and spreading, and the superior strain was selected, thereby obtaining the amino acid dehydrogenase mutant pDyGDH-F95L-A108T-R172P-R303H. And in the following experiments, all the other single mutants pDyGDH-A108T, pDyGDH-R172P and pDYGDH-R303H were constructed by the same method.

The mutation PCR system was as follows: 2×Phanta Max buffer 25 μL, dNTPs 1 μL, forward and reverse primers 1 μL respectively, template 1 μL, Phanta Super-Fidelity DNA polymerase 0.5 μL, and ddH$_2$O to a final volume of 50 μL. The conditions of the PCR procedure were as follows: pre-denaturation at 95° C. for 5 min; 30 cycles of 90° C. for 30 s, 62° C. for 30 s and 72° C. for 7 min, and finally extension at 72° C. for 5 min. The PCR result was checked by DNA agarose gel electrophoresis. The PCR product was digested with restriction endonuclease DpnI at 37° C. and 220 rpm for 1 h, the DpnI was heat inactivated at 65° C. for 1 min, the digested PCR product was transformed by heat shock treatment, competent *E. coli* BL21(DE3) was activated, cultured at 37° C. and 220 rpm for 1 h, then was spread onto an LB plate with 50 μg/mL ampicillin, and invertedly incubated overnight at 37° C., superior mutants were selected from the obtained mutants, sent to Hangzhou Qingke Biotechnology Co., Ltd. for sequencing confirmation and stored.

TABLE 1

Primers designing for the site-directed saturation mutagenesis of the amino acid dehydrogenase

| Primer | Primer sequence (5'-3') |
| --- | --- |
| F95 | F: GGTTTGCGTNNKCACCCTTCCGTGAATCT<br>R: GGAAGGGTGMNNACGCAAACCTCCCTTAT |
| A108 | F: AAATTCTTGNNKTTTGAACAAGTTTTTAAA<br>R: TTGTTCAAAMNNCAAGAATTTCAGTACAC |
| R172 | F: GTAGGAGCCNNKGAGATTGGGTTTATGTT<br>R: CCCAATCTCMNNGGCTCCTACTCCAATATC |
| R303 | F: CTGGAATTCNNKAAGGGCCAGA<br>R: CTGGCCCTTMNNGAATTCCAGACC |

Example 2: Induced Expression of the Original Amino Acid Dehydrogenase, its Mutant and the Glucose Dehydrogenase The gene of the glucose dehydrogenase esgdh (the nucleotide sequence was shown in SEQ ID No. 3, and the amino acid sequence was shown in SEQ ID No. 4) was cloned from *Exiguobacterium sibiricum* and connected to vector pET-28b (+) by double digestion, the recombinant plasmid was transformed into *E. coli* BL21(DE3), thereby obtaining a recombinant glucose dehydrogenase strain *E. coli* BL21(DE3)/pET28b-esgdh.

The original strain *E. coli* BL21(DE3)/pETDEut-dygdh and the strain containing the amino acid dehydrogenase mutant from Example 1 were respectively inoculated into LB liquid medium containing 50 μg/mL (final concentration) ampicillin, cultured at 37° C. for 8 hours, the resulting inoculum was inoculated with 2% incubating volume to fresh LB liquid medium containing 50 μg/mL (final concentration) ampicillin, cultured at 37° C. and 180 rpm for 1.5 h, then added with IPTG at a final concentration of 0.1 mM, cultured at 18° C. for 20 h, and centrifuged at 4° C. and 8000 rpm for 10 min, thereby obtaining respective wet cells.

The strain E. coli BL21(DE3)/pET28b-esgdh containing the recombinant glucose dehydrogenase was inoculated into LB liquid medium containing 50 μg/mL (final concentration) kanamycin, cultured at 37° C. for 8 hours, the resulting inoculum was inoculated with 2% incubating volume to fresh LB liquid medium containing 50 μg/mL (final concentration) kanamycin, cultured at 37° C. and 180 rpm for 1.5 h, then added with IPTG at a final concentration of 0.1 mM, cultured at 28° C. for 10 h, and centrifuged at 4° C. and 8000 rpm for 10 min, thereby obtaining wet cells containing glucose dehydrogenase.

The above cells with corresponding proteins can be used for preparation of pure protein enzyme liquid and used as crude enzyme for application in asymmetric reductive amination of 2-carbonyl-4-(hydroxymethylphosphinyl)-butyric acid to give L-glufosinate-ammonium.

Example 3: Screening of the Mutant Library

The wet cells of the mutant strain and that of the glucose dehydrogenase obtained by induced expression from Example 2 were mixed at the mass ratio of 3:1, and resuspended in a pH 7.4, 100 mM phosphate buffer at a ratio of 50 g of the total cell amount per liter, the resulting mixture was subjected to ultrasonication on an ice-water mixture for 15 minutes, the conditions of the ultrasonication were 400 W, 1 second on, and 5 seconds off, thereby obtaining crude enzyme liquid. Under the same conditions, the wet cells of the original strain E. coli BL21(DE3)/pET2Deut-dygdh was used to replace that of the mutant strain to prepare crude enzyme liquid of the original strain.

The crude enzyme liquid of the mutant strain or the original strain was used as a catalyst, 2-carbonyl-4-(hydroxymethylphosphinyl)-butyric acid was used as a substrate, glucose was used as an auxiliary substrate, and the endogenous NADPH in the cells rather than exogenous NADPH or NADP+ were used to establish a coenzyme circulatory system. The reaction system was selected as 10 mL, the amount of catalyst was 50 g of the wet cells before ultrasonication per liter, the final concentration of substrate was 300 mM, and the final concentration of glucose was 450 mM, after the reaction was carried out at 30° C. and 600 rpm for 10 min, 100 μL of the reacting solution was taken and added with 5 μL of hydrochloric acid to end the reaction, and then added with ultrapure water to a final volume of 1 mL, that was, the reaction solution was diluted 10 times, the diluted reaction solution was first subjected to derivatization treatment: 200 μl of the diluted reacting solution+400 μL derivatization reagent (a pH 9.8 borate buffer containing 15 mM o-phthalaldehyde and 15 mM N-acetyl-L-cysteine) were subjected to derivatization for 5 min at 30° C., 400 μL of ultrapure water was added to a final volume of 1 mL, the resulting mixture was centrifuged for 1 min at 12000 rpm, the supernatant was passed through a 0.22 μm membrane filter, the filtrate was taken as a liquid sample, and HPLC was used to detect 2-carbonyl-4-(hydroxymethylphosphinyl)-butyric acid, L-glufosinate-ammonium, D-glufosinate-ammonium and $de_p$ values. Using the product L-glufosinate-ammonium and e.e. as indicators, superior mutants were screened, and the experimental results were shown in Table 2.

HPLC conditions of detecting 2-carbonyl-4-(hydroxymethylphosphinyl)-butyric acid were as follows: the chromatographic column was Unitary® C18 (4.6×250 mm, Acchrom, China), the mobile phase was acetonitrile: 50 mM ammonium dihydrogen phosphate (pH3.8, containing 10% tetrabutylammonium hydroxide) at a volume ratio of 12:88. The flow rate was 1.0 mL/min, the test wavelength was 232 nm, the injection volume was 10 μL, the column temperature was 30° C., and the retention time of 2-carbonyl-4-(hydroxymethylphosphinyl)-butyric acid was 9.7 min.

HPLC conditions of detecting glufosinate-ammonium: the chromatographic column was Unitary® C18 (4.6×250 mm, Acchrom, China), the mobile phase was methanol: 0.05M ammonium acetate (pH5.7) at a volume ratio of 10:90. The flow rate was 1.0 mL/min, the test wavelength Ex=232 nm, the injection volume was 10 μL, the column temperature was 30° C., and the retention time of L-glufosinate-ammonium and D-glufosinate-ammonium was 10.6 min and 12.6 min respectively.

TABLE 2

Catalytic performance and stereoselectivity of pDyGDH and its mutants

| Strains | L-glufosinate-ammonium (mM) $^a$ | e.e. (%) |
|---|---|---|
| pDyGDH | 39.4 ± 0.6 | 99.5 |
| pDyGDH-F95L | 145.2 ± 0.6 | 99.5 |
| pDyGDH-F95I | 247.2 ± 0.6 | 99.5 |
| pDyGDH-F95A | 38.3 ± 2.2 | 99.5 |
| pDyGDH-F95W | 30.2 ± 0.7 | 99.5 |
| pDyGDH- F95I-A108T | 255.6 ± 1.2 | 99.5 |
| pDyGDH- F95I-A108F | 20.8 ± 0.8 | 99.5 |
| pDyGDH- F95I-A108H | 30.0 ± 0.1 | 99.5 |
| pDyGDH- F95I-A108D | 15.2 ± 3.1 | 99.5 |
| pDyGDH- F95I-A108C | 10.2 ± 0.1 | 99.5 |
| pDyGDH- F95I-A108S | 252.6 ± 2.0 | 99.5 |
| pDyGDH- F95I-A108Y | 51.8 ± 2.0 | 99.5 |
| pDyGDH- F95I-R172P | 252.9 ± 0.9 | 99.5 |
| pDyGDH- F95I-R172V | 250.5 ± 1.8 | 99.5 |
| pDyGDH- F95I-R172A | 38.4 ± 1.6 | 99.5 |
| pDyGDH- F95I-R172N | 35.5 ± 0.7 | 99.5 |
| pDyGDH- F95I- R172K | 39.0 ± 0.3 | 99.5 |
| pDyGDH- F95I-R172D | 19.8 ± 1.7 | 99.5 |
| pDyGDH- F95I-R172H | 31.0 ± 0.6 | 99.5 |
| pDyGDH- F95I-R172S | 45.1 ± 1.1 | 99.5 |
| pDyGDH- F95I-A108T-R172P | 272.1 ± 1.2 | 99.5 |
| pDyGDH- F95I-A108T-R172V | 255.4 ± 2.3 | 99.5 |
| pDyGDH- F95I-A108S-R172P | 263.5 ± 0.7 | 99.5 |
| pDyGDH-F95I-108T-R172P-R303H | 285.3 ± 2.4 | 99.5 |

Example 4: Purification of the Original Amino Acid Dehydrogenase and its Mutants The superior mutants obtained in Example 3(pDyGDH-F95I, pDyGDH-A108T, pDyGDH-R172P, pDyGDH-R303H, pDyGDH-F95I-A108T, pDyGDH-F95I-A108T-R172P, pDyGDH-F95I-A108T-R172P-R303H) were used to obtain wet cells of the amino acid dehydrogenase mutants according to the method in Example 2, the wet cells were respectively suspended in buffer A (pH 8.0, 50 mM sodium phosphate buffer containing 0.3 M NaCl and 30 mM imidazole), subjected to sonication for 20 min (ice bath, 400 W, 1 second on and 5 seconds off), and centrifuged for 20 min at 4° C. and 12000 rpm, then the supernatant was collected. The mutant proteins were purified by Ni-NTA column (1.6×10 cm, Bio-Rad, the USA), and the specific operation was carried out as follows: ① a Ni column was equilibrated with 5 column volumes of binding buffer (pH 8.0, 50 mM sodium phosphate buffer containing 0.3 M NaCl) until the baseline was steady; ② the sample was loaded with a flow rate of 1 mL/min, the amount of the loading sample was 25-40 mg/mL calculated by the volume of the column, thereby attaching the target protein to the Ni column; ③ the column was washed with 6 column volumes of buffer A (pH 8.0, 50 mM sodium phosphate buffer containing 0.3 M NaCl and 30 mM imidazole) at a flow rate of 1 mL/min until the baseline was steady; ④ the column was washed with buffer B (pH 8.0, 50 mM sodium phosphate buffer containing 0.3 M NaCl and 500 mM imidazole) at a flow rate of 1 mL/min, the target protein was collected and dialyzed overnight in a pH 7.5, 20 mM phosphate buffer, thereby obtaining the pure enzyme; and ⑤ the Ni column was washed with 5 column volumes of binding buffer (pH 8.0, 50 mM sodium phosphate buffer containing 0.3 M NaCl) until the baseline was steady, and the Ni column was stored in 5 column volumes of ultrapure water containing 20% ethanol.

The pure amino acid dehydrogenase of the original strain E. coli BL21(DE3)/pETDEut-pdygdh was collected by the same conditions.

Example 5: Specific Enzyme Activity Determination of the Original Amino Acid Dehydrogenase and its Mutants The enzyme activity unit (U) is defined as follows: under the conditions of 35° C. and pH 7.4, the amount of enzyme required for producing 1 μmol L-glufosinate-ammonium in one minute is one enzyme activity unit, U. Specific enzyme activity is defined as activity units of one milligram of enzyme protein, U/mg.

Standard conditions of enzyme activity detection: 100 mM 2-carbonyl-4-(hydroxymethylphosphinyl)-butyric acid, 10 mM NADPH, 0.02 ug/uL enzyme liquid, 30° C., pH 7.4 and 600 rpm for 10 min, the resulting sample was treated and then analyzed by HPLC.

The protein concentration was determined by BCA protein determination kit (NanJing Key Gen Biotech Co., Ltd, NanJing).

Specific enzyme activity of the original amino acid hydrogenase and its mutants was shown in Table 3.

TABLE 3

| Enzyme | Relative activity (%) | e.e. (%) |
|---|---|---|
| pDyyGDH | 100[a] | 99.5 |
| pDyGDH-F95I | 411.1 ± 4.2 | 99.5 |
| pDyGDH-A108T | 398.1 ± 2.1 | 99.5 |
| pDyGDH-R172P | 417.3 ± 8.0 | 99.5 |
| pDyGDH-R303H | 418.0 ± 7.3 | 99.5 |
| pDyGDH- F95I-A108T | 531.0 ± 10.0 | 99.5 |
| pDyGDH-F95I-A108T-R172P | 1171.6 ± 1.1 | 99.5 |
| pDyGDH- F95I-A108T-R172P-R303H | 3320 ± 3.2 | 99.5 |

[a] under standard conditions, the primary enzyme actively of pDyGDH is defined as 100%

Example 6: Kinetic Parameter Determination of the Original Amino Acid Dehydrogenase and its Mutants Kinetic parameters of the amino acid hydrogenase and its mutants were examined, 2-carbonyl-4-(hydroxymethylphosphinyl)-butyric acid was taken as substrate, the concentration was set as 2-10 mM (2, 4, 6, 8, 10 mM), the concentration of exogenous coenzyme NADPH was set as 1-5 mM (1, 2, 3, 4, 5 mM), 100 uL of pure enzyme solution was added (according to Example 4).

The reaction system was 500 μL, the pure enzyme solution collected in Example 4 was diluted 10 times with pH 7.4, 100 mM phosphate buffer, then 100 μL of the resulting solution was sampled, added with the substrate and exogenous coenzyme NADPH, pH 7.4, 100 mM phosphate buffer was taken as a reaction medium, after reacting at 35° C. and 600 rpm for 10 min, the concentration of L-glufosinate-ammonium in the reacting solution was determined by HPLC (according to Example 4).

According to the sequential mechanism of amino acid dehydrogenase's catalytic reaction, $v_{max}$, $K_m^A$, $K_m^B$ can be calculated by dual-reciprocal graph, the results were shown in Table 4. By comparing $k_{cat}$ and $K_m$, it can be found that the Km values of pDyGDH on 2-carbonyl-4-(hydroxymethylphosphinyl)-butyric acid and NADPH were 3.45 mM and 0.11 mM respectively. Except for the mutant pDyGDH-A08T, the rest of the mutants had a certain decrease which meant an increase of the affinity with 2-carbonyl-4-(hydroxymethylphosphinyl)-butyric acid and NADPH. The catalytic efficiency $k_{cat}/K_m^B$ of the mutant pDyGDH-F95I-A108T-R172P-R303H on 2-carbonyl-4-(hydroxymethylphosphinyl)-butyric acid reached 363.1 s$^{-1}$·mM$^{-1}$, which was 29.3 times higher than that of the original enzyme ($k_{cat}/K_m^B$=12.41 s$^{-1}$·mM$^{-1}$), and its catalytic efficiency on coenzyme NADPH reached 14382.3 s$^{-1}$·mM$^{-1}$, which was 37.3 times higher than that of the original enzyme ($k_{cat}/K_m^B$=385.67 s$^{-1}$·mM$^{-1}$).

TABLE 4

Comparison of kinetic parameter of the original pDyGDH and its mutants

| Enzyme | $k_{cat}$ (s$^{-1}$)[a] | $K_m^A$ (mM)[b] | $K_m^B$ (mM)[b] | $k_{cat}/K_m^A$ (s$^{-1}$·mM$^{-1}$) | $k_{cat}/K_m^B$ (s$^{-1}$·mM$^{-1}$) |
|---|---|---|---|---|---|
| original pDyGDH | 42.81 ± 3.10 | 0.11 | 3.45 | 385.67 | 12.41 |
| pDyGDH-F95I | 45.01 ± 2.91 | 0.092 | 2.67 | 489.23 | 16.85 |
| pDyGDH-A108T | 33.80 ± 2.21 | 0.16 | 4.91 | 209.93 | 6.88 |
| pDyGDH-R172P | 50.98 ± 1.04 | 0.071 | 2.12 | 718.03 | 24.05 |
| pDyGDH-R303H | 48.21 ± 0.98 | 0.090 | 3.30 | 535.67 | 14.61 |
| pDyGDH-F95I-A108T | 53.45 ± 4.01 | 0.097 | 3.01 | 551.03 | 17.75 |
| pDyGDH-F95I-A108T-R172P | 651.9 ± 3.12 | 0.046 | 2.19 | 14171.7 | 297.7 |
| pDyGDH-F95I-A108T-R172P-R303H | 733.5 ± 3.83 | 0.051 | 2.02 | 14382.3 | 363.1 |

Figure 1:
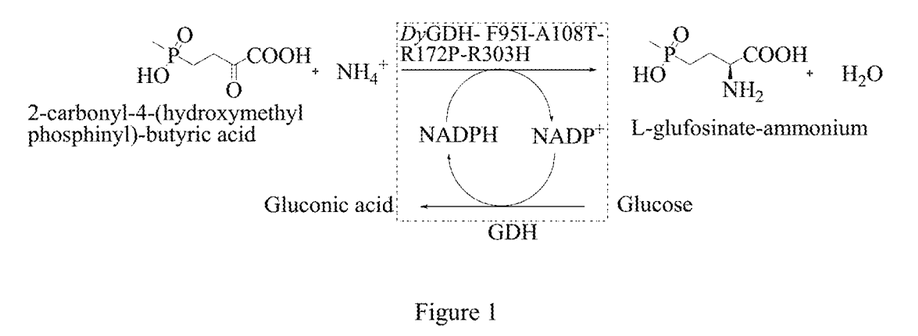
FIG. 1 is a diagram of the reaction that the amino acid dehydrogenase mutant DyGDH-F95I-A108T-R172P-R303H coupled with the glucose dehydrogenase catalyzes the asymmetric reductive amination of 2-carbonyl-4-(hydroxymethylphosphinyl)-butyric acid to L-glufosinate-ammonium.
Figure 2:
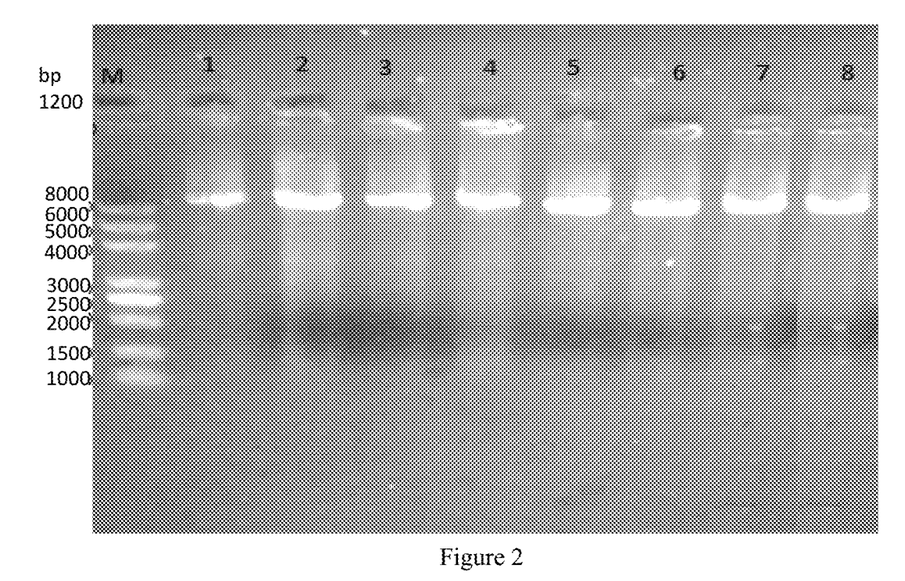
FIG. 2 is a nucleic acid electrophoresis diagram of a site-directed saturation mutagenesis of the amino acid dehydrogenase, wherein M: Molecular weight of standard nucleic acid; Lane 1: pETDEut-dygdh-F95L; Lane 2: pETDEut-dygdh-F108L; Lane 3: pETDEut-dygdh-A108T; Lane 4: pETDEut-dygdh-R172P; Lane 5: pETDEut-dygdh-R303H; Lane 6: pETDEut-dygdh-F95L-A108T; Lane 7: pETDEut-dygdh-F95L-A108T-R172P; and Lane 8: pETDEut-dygdh-F95L-A108T-R172P-R303H.
Figure 3:
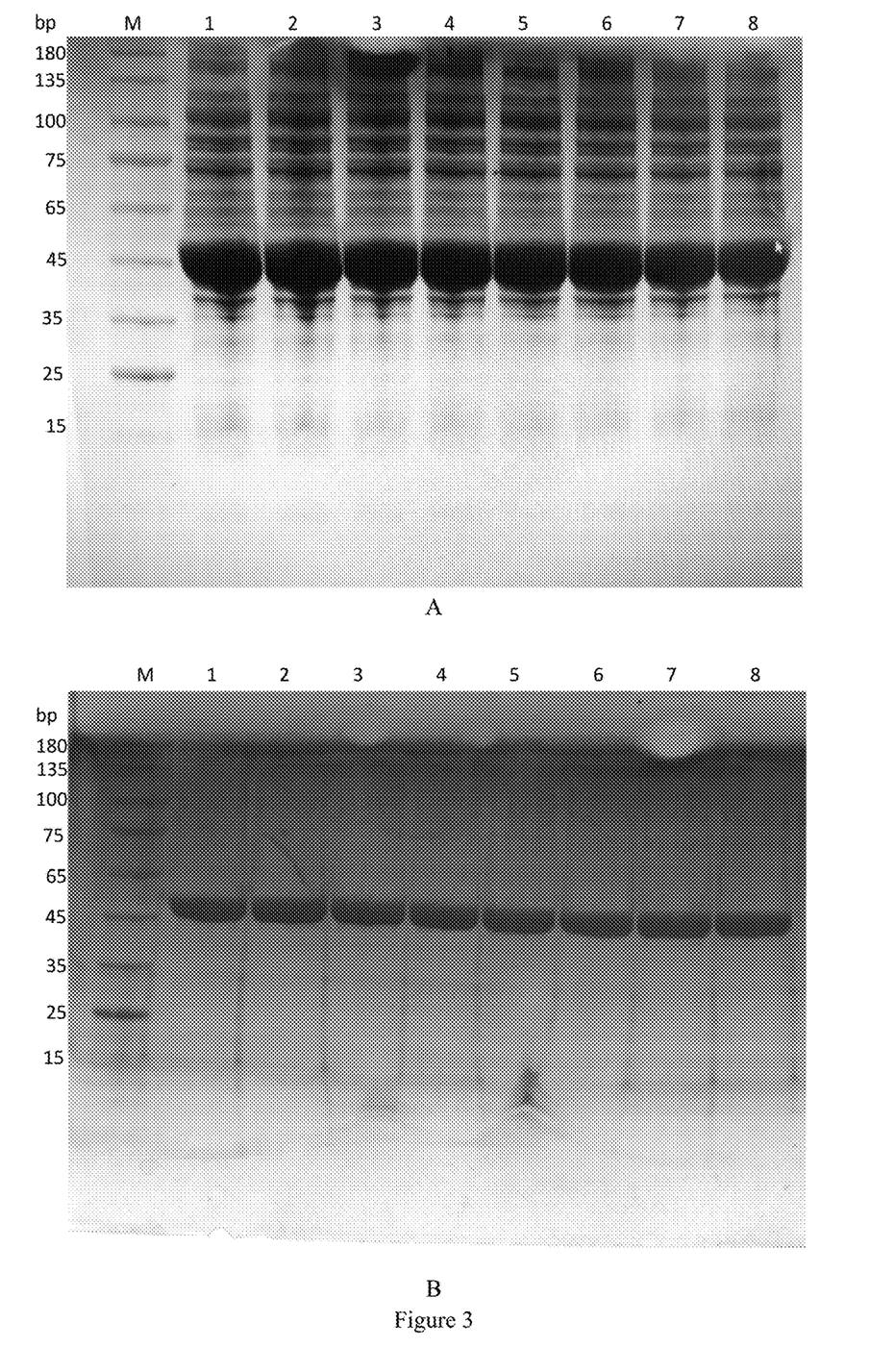
FIG. 3 is an SDS-PAGE diagram of a crude enzyme solution (A) and a pure enzyme solution (B) of the amino acid dehydrogenase mutant, wherein M: Molecular weight of standard nucleic acid; Lane 1: Maternal amino acid dehydrogenase; Lane 2: pDyGDH-F95L; Lane 3: pDyGDH-A108T; Lane 4: pDyGDH-R172P; Lane 5: pDyGDH-R303H; Lane 6: pDyGDH-F95L-A108T; Lane 7: pDyGDH-F95L-A108T-R172P; and Lane 8: pDyGDH-F95L-A108T-R172P-R303H.
Figure 4:
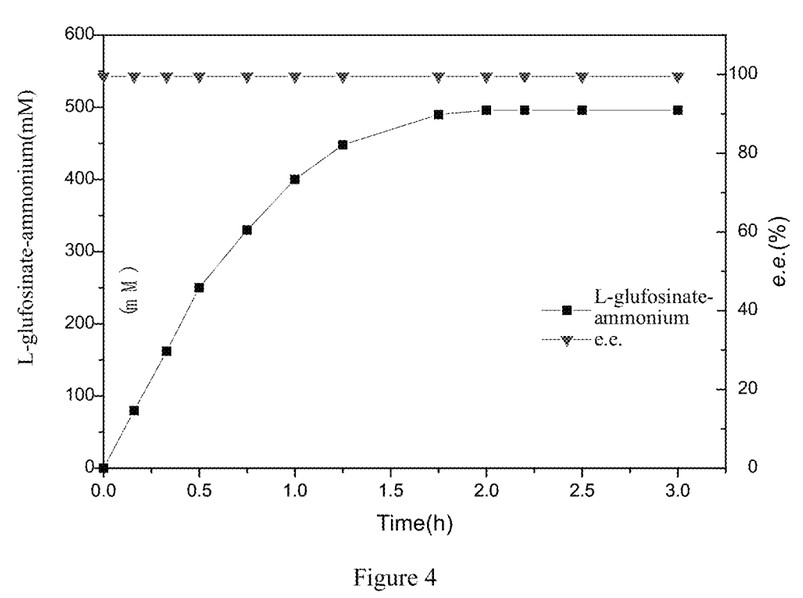
FIG. 4 is a timeline infographic showing that the amino acid dehydrogenase mutant coupled with EsGDH catalyzes the asymmetric reductive amination of 2-carbonyl-4-(hydroxymethylphosphinyl)-butyric acid to L-glufosinate-ammonium.

Example 7: Asymmetric Reductive Amination of 2-carbonyl-4-(hydroxymethylphosphinyl)-butyric Acid Using the Amino Acid Dehydrogenase Mutant pDyGDH-F95I-A108T-R172P-R303H According to Example 2, 3 g of the cells of the amino acid dehydrogenase mutant pDyGDH-F95I-A108T-R172P-R303H and 1 g of the cells of the glucose dehydrogenase EsGDH cells obtained by fermentation were mixed and resuspended in 40 mL of the pH 7.4, 100 mM phosphate buffer, the resulting mixture was subjected to ultrasonication on ice (the conditions of the ultrasonication are 400 W, 1 second on, and 5 seconds off), all the broken mixture (crude enzyme liquid) was added with 2-carbonyl-4-(hydroxymethylphosphinyl)-butyric acid at a final concentration of 500 mM and glucose at a final concentration of 750 mM, thereby constructing the reaction system with a volume of 50 ml, the reaction was carried out at 35° C. and 300 rpm, ammonia water was flow-added to maintain the pH of the reaction solution at 7.4. The liquid phase method shown in Example 3 was used to detect the synthesis of the product L-glufosinate-ammonium and the change of e.e. value during the reaction, and the reaction processing curve was shown in FIG. 4. The figure showed that the concentration of the product gradually increased with time, the reaction was completed within 120 minutes, the substrate conversion rate was more than 99%, and the product e.e. value was always more than 99.5%.

---

The invention claimed is:

1. An amino acid dehydrogenase mutant, wherein the amino acid dehydrogenase mutant is obtained by a single mutation or multi-site mutations of the amino acid at position 95, 108, 172, 303 of the amino acid sequence shown in SEQ ID NO: 2, wherein the single mutation or the multi-site mutations is/are selected from the group consisting of:
   (1) phenylalanine at position 95 of the amino acid sequence shown in SEQ ID NO: 2 into leucine or isoleucine;
   (2) phenylalanine at position 95 of the amino acid sequence shown in SEQ ID NO: 2 into leucine, and alanine at position 108 into threonine, serine or tyrosine;
   (3) phenylalanine at position 95 of the amino acid sequence shown in SEQ ID NO: 2 into isoleucine, and arginine at position 172 into proline or valine;
   (4) phenylalanine at position 95 of the amino acid sequence shown in SEQ ID NO: 2 into isoleucine, alanine at position 108 into threonine, and arginine at position 172 into proline or valine;
   (5) phenylalanine at position 95 of the amino acid sequence shown in SEQ ID NO: 2 into isoleucine, alanine at position 108 into tyrosine, and arginine at position 172 into proline; and
   (6) phenylalanine at position 95 of the amino acid sequence shown in SEQ ID NO: 2 into isoleucine, alanine at position 108 into threonine, arginine at position 172 into proline and arginine at position 303 into histidine.

2. The amino acid dehydrogenase mutant as claimed in claim 1, wherein the amino acid dehydrogenase mutant is obtained by mutating phenylalanine at position 95 of the amino acid sequence shown in SEQ ID NO: 2 into isoleucine, alanine at position 108 into threonine, arginine at position 172 into proline and arginine at position 303 into histidine.

3. A method of performing asymmetric reductive amination of 2-carbonyl-4-(hydroxymethylphosphinyl)-butyric acid to L-glufosinate-ammonium, the method comprising contacting the amino acid dehydrogenase mutant as claimed in claim 1 with 2-carbonyl-4-(hydroxymethylphosphinyl)-butyric acid.

4. The method as claimed in claim 3, wherein the method is carried out as follows: wet cells obtained by induction of a recombinant genetically engineered strain containing the gene of the amino acid dehydrogenase mutant and wet cells obtained by induction of an engineered strain containing the gene of the glucose dehydrogenase are mixed and resuspended in a pH7.4, 100 mM phosphate buffer, the resulting mixture is subjected to ultrasonication and centrifugation, then the resulting supernatant is used as catalyst, 2-carbonyl-4-(hydroxymethylphosphinyl)-butyric acid is used as substrate and glucose is used as auxiliary substrate, a reaction is carried out under the conditions of 35° C. and 400-600 rpm, after the reaction is completed, the reaction solution is separated and purified to obtain L-glufosinate-ammonium.

5. The method as claimed in claim 4, wherein in the reaction, the final concentration of 2-carbonyl-4-(hydroxymethylphosphinyl)-butyric acid is 300-500 mM, the final concentration of glucose is 450-750 mM, the amount of the catalyst is 50-100 g/L calculated by the total amount of the wet cells before ultrasonication, the wet cells obtained by induction of the recombinant genetically engineered strain containing the gene of the amino acid dehydrogenase mutant and the wet cells obtained by induction of engineered strain containing the gene of the glucose dehydrogenase are mixed at the mass ratio of 3:1.

6. The method as claimed in claim 4, wherein the wet cells containing the amino acid dehydrogenase mutant are prepared by a method as follows: the recombinant genetically engineered strain containing the gene of the amino acid dehydrogenase mutant is inoculated into LB liquid medium containing 50 g/mL (final concentration) ampicillin, cultured at 37° C. for 8 hours, the resulting inoculum is inoculated with 2% incubating volume to fresh LB liquid medium containing 50 g/mL (final concentration) ampicillin, cultured at 37° C. and 180 rpm for 1.5 h, then added with IPTG at a final concentration of 0.1 mM, cultured at 18° C. for 20 h, and centrifuged at 4° C. and 8000 rpm for 10 min, thereby obtaining the wet cells containing the amino acid dehydrogenase mutant; the wet cells containing the glucose dehydrogenase are prepared by the following method: the engineered strain containing the gene of the glucose dehydrogenase is inoculated into LB liquid medium containing 50 g/mL (final concentration) kanamycin, cultured at 37° C. for 9 hours, the resulting inoculum is inoculated with 2% incubating volume to fresh LB liquid medium containing 50 g/mL (final concentration) kanamycin, cultured at 37° C. and 180 rpm for 1.5 h, then added with IPTG at a final concentration of 0.1 mM, cultured at 28° C. for 10 h, and centrifuged at 4° C. and 8000 rpm for 10 min, thereby obtaining the wet cells containing the glucose dehydrogenase.

7. The method as claimed in claim 4, wherein the ultrasonication is carried out as follows: the wet cells obtained by induction of the recombinant genetically engineered strain containing the gene of the amino acid dehydrogenase mutant and the wet cells obtained by induction of engineered strain containing the gene of the glucose dehydrogenase are mixed and resuspended in the pH7.4, 100 mM phosphate buffer, the resulting mixture is subjected to ultrasonication for 15 min, and the conditions of the ultrasonication are 400 W, 1 second on, and 5 seconds off.

\* \* \* \* \*

SEQUENCE LISTING

```
<160> NUMBER OF SEQ ID NOS: 12

<210> SEQ ID NO 1
<211> LENGTH: 1355
<212> TYPE: DNA
<213> ORGANISM: Pseudomonas monteilii

<400> SEQUENCE: 1
gagctcatga ttgaaagcgt cgactcattt ttagcacgct acaacaacg cgatccaggt    60 caacctgagt tcaccaagc cgtggaggaa gttctgcgca cgttgtggcc gtttctggaa   120
gccaacccgc gctatttgca aagcggtatc ctggaacgta tggtcgagcc agaacgtgct   180
gtcttgtttc gcgtaagctg ggtagacgac caagggaaag ttcaggtgaa ccgtggttat   240
cgtattcaaa tgagcagcgc gattggaccc tataagggag gtttgcgttt tcacccttcc   300
gtgaatctga gtgtactgaa attcttggcc tttgaacaag tttttaaaaa ttcgctgact   360
tcccttccta tgggagggggg taagggggga tctgattttg atccgaaggg taaatctgac   420
gcggaggtaa tgcgcttttg ccaggcgttt atgtcggagt tgtaccgcca cattgggccg   480
gactgcgacg tgccagcggg ggatattgga gtaggagccc gcgagattgg gtttatgttc   540
ggacaataca agcgtttggc aaatcaattc acatcggttt tgaccgggaa agggatgacg   600 tatggggggca gtttaattcg tcctgaagca acgggatacg gttgcgtata cttcgcggag   660
gaaatgctta aacgtcaagg ccttcgcgta gatggccgcc gcgttgctat cagcggctct   720
gggaacgtcg ctcagtatgc agcgcgcaaa gtgatggact tgggcggcaa agtcatctct   780 cttttccgatt cggaaggtac cttatatgca gagggtgggt tgaccgaagc acaatggaaa   840
gcggtgatgc aattgaaaaa cgtagcgcgc ggacgcattt cagagcttgc tgaagccttc   900
ggtctggaat tccgcaaggg ccagactccg tggagcttac catgtgacat tgcattgccg   960
tgtgcgacgc aaaatgagct gggtatcgaa gatgcgcgca cccttcttcg caatggttgt  1020
atttgcgtgg ctgagggagc taatatgccg acgacgttgg ccgcggtgga cctgttcatc  1080
gacgctggta tcctttatgc accgggaaag gcaagtaacg ctggcggtgt ggccgtttcg  1140
gggttagaga tgagtcaaaa cgcgatgcgt cttctttgga cagcgggcga agtcgatagc  1200
aagttgcata atattatgca gtccattcac catgcctgtg ttcactatgg tgaggaggct  1260
gacggaaaag tgaattacgt taaaggagct aacattgcgg gctttgttaa agtcgccgac  1320
gcaatgcttg cccagggagt agtctaagcg gccgc                             1355

<210> SEQ ID NO 2
<211> LENGTH: 446
<212> TYPE: PRT
<213> ORGANISM: Pseudomonas monteilii
```

<400> SEQUENCE: 2

```
Met Ile Glu Ser Val Asp Ser Phe Leu Ala Arg Leu Gln Gln Arg Asp
1               5                   10                  15

Pro Gly Gln Pro Glu Phe His Gln Ala Val Glu Val Leu Arg Thr
            20                  25                  30

Leu Trp Pro Phe Leu Glu Ala Asn Pro Arg Tyr Leu Gln Ser Gly Ile
        35                  40                  45

Leu Glu Arg Met Val Glu Pro Glu Arg Ala Val Leu Phe Arg Val Ser
    50                  55                  60

Trp Val Asp Asp Gln Gly Lys Val Gln Val Asn Arg Gly Tyr Arg Ile
65                  70                  75                  80

Gln Met Ser Ser Ala Ile Gly Pro Tyr Lys Gly Gly Leu Arg Phe His
                85                  90                  95

Pro Ser Val Asn Leu Ser Val Leu Lys Phe Leu Ala Phe Glu Gln Val
                100                 105                 110

Phe Lys Asn Ser Leu Thr Ser Leu Pro Met Gly Gly Gly Lys Gly Gly
            115                 120                 125

Ser Asp Phe Asp Pro Lys Gly Lys Ser Asp Ala Glu Val Met Arg Phe
130                 135                 140

Cys Gln Ala Phe Met Ser Glu Leu Tyr Arg His Ile Gly Ala Asp Cys
145                 150                 155                 160

Asp Val Pro Ala Gly Asp Ile Gly Val Gly Ala Arg Glu Ile Gly Phe
                165                 170                 175

Met Phe Gly Gln Tyr Lys Arg Leu Ala Asn Gln Phe Thr Ser Val Leu
            180                 185                 190

Thr Gly Lys Gly Met Thr Tyr Gly Gly Ser Leu Ile Arg Pro Glu Ala
        195                 200                 205

Thr Gly Tyr Gly Cys Val Tyr Phe Ala Glu Met Leu Lys Arg Gln
    210                 215                 220

Gly Leu Arg Val Asp Gly Arg Val Ala Ile Ser Gly Ser Gly Asn
225                 230                 235                 240

Val Ala Gln Tyr Ala Ala Arg Lys Val Met Asp Leu Gly Gly Lys Val
                245                 250                 255

Ile Ser Leu Ser Asp Ser Glu Gly Thr Leu Tyr Ala Glu Gly Gly Leu
            260                 265                 270

Thr Glu Ala Gln Trp Glu Ala Val Met Gln Leu Lys Asn Val Ala Arg
        275                 280                 285

Gly Arg Ile Ser Glu Leu Ala Glu Ala Phe Gly Leu Glu Phe Arg Lys
    290                 295                 300

Gly Gln Thr Pro Trp Ser Leu Pro Cys Asp Ile Ala Leu Pro Cys Ala
305                 310                 315                 320

Thr Gln Asn Glu Leu Gly Ile Glu Asp Ala Arg Thr Leu Leu Arg Asn
                325                 330                 335

Gly Cys Ile Cys Val Ala Glu Gly Ala Asn Met Pro Thr Thr Leu Ala
            340                 345                 350

Ala Val Asp Leu Phe Ile Asp Ala Gly Ile Leu Tyr Ala Pro Gly Lys
        355                 360                 365

Ala Ser Asn Ala Gly Gly Val Ala Val Ser Gly Leu Glu Met Ser Gln
    370                 375                 380

Asn Ala Met Arg Leu Leu Trp Thr Ala Gly Glu Val Asp Ser Lys Leu
385                 390                 395                 400

His Asn Ile Met Gln Ser Ile His His Ala Cys Val His Tyr Gly Glu
```

```
                    405                 410                 415
Glu Ala Asp Gly Lys Val Asn Tyr Val Lys Gly Ala Asn Ile Ala Gly
            420                 425                 430

Phe Val Lys Val Ala Asp Ala Met Leu Ala Gln Gly Val Val
            435                 440                 445

<210> SEQ ID NO 3
<211> LENGTH: 789
<212> TYPE: DNA
<213> ORGANISM: Exiguobacterium sibiricum

<400> SEQUENCE: 3
atgggttata attctctgaa aggcaaagtc gcgattgtta ctggtggtag catgggcatt      60
ggcgaagcga tcatccgtcg ctatgcagaa gaaggcatgc gcgttgttat caactatcgt     120
agccatccgg aggaagccaa aaagatcgcc gaagatatta acaggcagg tggtgaagcc      180 ctgaccgtcc agggtgacgt ttctaaagag gaagacatga tcaacctggt gaaacagact     240
gttgatcact tcggtcagct ggacgtcttt gtgaacaacg ctggcgttga atgccttct      300 ccgtcccacg aaatgtccct ggaagactgg cagaaagtga tcgatgttaa tctgacgggt     360
gcgttcctgg cgctcgtga agctctgaaa tacttcgttg aacataacgt gaaaggcaac     420
attatcaata tgtctagcgt ccacgaaatc atcccgtggc ctactttcgt acattacgct     480
gcttctaagg gtgcgttaa actgatgacc agactctgg ctatggaata tgcaccgaaa      540
ggtatccgca ttaacgctat cggtccaggc gcgatcaaca ctccaattaa tgcagaaaaa     600
ttcgaggatc cgaaacagcg tgcagacgtg aaaagcatga tcccgatggg caacatcggc     660
aagccagagg agatttccgc tgtcgcggca tggctggctt ctgacgaagc gtcttacgtt     720
accggcatca ccctgttcgc agatggtggc atgaccctgt acccgagctt tcaggctggc     780
cgtggttga                                                           789

<210> SEQ ID NO 4
<211> LENGTH: 262
<212> TYPE: PRT
<213> ORGANISM: Exiguobacterium sibiricum

<400> SEQUENCE: 4

Met Gly Tyr Asn Ser Leu Lys Gly Lys Val Ala Ile Val Thr Gly Gly
1               5                   10                  15

Ser Met Gly Ile Gly Glu Ala Ile Ile Arg Arg Tyr Ala Glu Glu Gly
            20                  25                  30

Met Arg Val Val Ile Asn Tyr Arg Ser His Pro Glu Glu Ala Lys Lys
        35                  40                  45

Ile Ala Glu Asp Ile Lys Gln Ala Gly Gly Glu Ala Leu Thr Val Gln
    50                  55                  60

Gly Asp Val Ser Lys Glu Glu Asp Met Ile Asn Leu Val Lys Gln Thr
65                  70                  75                  80

Val Asp His Phe Gly Gln Leu Asp Val Phe Val Asn Asn Ala Gly Val
                85                  90                  95

Glu Met Pro Ser Pro Ser His Glu Met Ser Leu Glu Asp Trp Gln Lys
            100                 105                 110

Val Ile Asp Val Asn Leu Thr Gly Ala Phe Leu Gly Ala Arg Glu Ala
        115                 120                 125

Leu Lys Tyr Phe Val Glu His Asn Val Lys Gly Asn Ile Ile Asn Met
    130                 135                 140
```

-continued

```
Ser Ser Val His Glu Ile Ile Pro Trp Pro Thr Phe Val His Tyr Ala
145                 150                 155                 160

Ala Ser Lys Gly Gly Val Lys Leu Met Thr Gln Thr Leu Ala Met Glu
            165                 170                 175

Tyr Ala Pro Lys Gly Ile Arg Ile Asn Ala Ile Gly Pro Gly Ala Ile
        180                 185                 190

Asn Thr Pro Ile Asn Ala Glu Lys Phe Glu Asp Pro Lys Gln Arg Ala
    195                 200                 205

Asp Val Glu Ser Met Ile Pro Met Gly Asn Ile Gly Lys Pro Glu Glu
210                 215                 220

Ile Ser Ala Val Ala Ala Trp Leu Ala Ser Asp Glu Ala Ser Tyr Val
225                 230                 235                 240

Thr Gly Ile Thr Leu Phe Ala Asp Gly Gly Met Thr Leu Tyr Pro Ser
            245                 250                 255

Phe Gln Ala Gly Arg Gly
            260
```

```
<210> SEQ ID NO 5
<211> LENGTH: 29
<212> TYPE: DNA
<213> ORGANISM: Artificial Sequence
<220> FEATURE:
<223> OTHER INFORMATION: Primer F95F
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (12)..(12)
<223> OTHER INFORMATION: k is g, or t

<400> SEQUENCE: 5
ggtttgcgtn nkcacccttc cgtgaatct                                    29

<210> SEQ ID NO 6
<211> LENGTH: 29
<212> TYPE: DNA
<213> ORGANISM: Artificial Sequence
<220> FEATURE:
<223> OTHER INFORMATION: Primer F95R
<220> FEATURE:
<221> NAME/KEY: misc_feature
<222> LOCATION: (10)..(10)
<223> OTHER INFORMATION: m is a, or c
<220> FEATURE:
<221> NAME/KEY: misc_feature
<222> LOCATION: (11)..(12)
<223> OTHER INFORMATION: n is a, c, g, or t

<400> SEQUENCE: 6
ggaagggtgm nnacgcaaac ctcccttat                                    29

<210> SEQ ID NO 7
<211> LENGTH: 30
<212> TYPE: DNA
<213> ORGANISM: Artificial Sequence
<220> FEATURE:
<223> OTHER INFORMATION: Primer A108F
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (12)..(12)
<223> OTHER INFORMATION: k is g, or t
```

<400> SEQUENCE: 7
aaattcttgn nktttgaaca agtttttaaa                                    30

<210> SEQ ID NO 8
<211> LENGTH: 29
<212> TYPE: DNA
<213> ORGANISM: Artificial Sequence
<220> FEATURE:
<223> OTHER INFORMATION: Primer A108R
<220> FEATURE:
<221> NAME/KEY: misc_feature
<222> LOCATION: (10)..(10)
<223> OTHER INFORMATION: m is a, or c
<220> FEATURE:
<221> NAME/KEY: misc_feature
<222> LOCATION: (11)..(12)
<223> OTHER INFORMATION: n is a, c, g, or t

<400> SEQUENCE: 8
ttgttcaaam nncaagaatt tcagtacac                                     29

<210> SEQ ID NO 9
<211> LENGTH: 29
<212> TYPE: DNA
<213> ORGANISM: Artificial Sequence
<220> FEATURE:
<223> OTHER INFORMATION: Primer R172F
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (12)..(12)
<223> OTHER INFORMATION: k is g, or t

<400> SEQUENCE: 9
gtaggagccn nkgagattgg gtttatgtt                                     29

<210> SEQ ID NO 10
<211> LENGTH: 30
<212> TYPE: DNA
<213> ORGANISM: Artificial Sequence
<220> FEATURE:
<223> OTHER INFORMATION: Primer R172R
<220> FEATURE:
<221> NAME/KEY: misc_feature
<222> LOCATION: (10)..(10)
<223> OTHER INFORMATION: m is a, or c
<220> FEATURE:
<221> NAME/KEY: misc_feature
<222> LOCATION: (11)..(12)
<223> OTHER INFORMATION: n is a, c, g, or t

<400> SEQUENCE: 10
cccaatctcm nnggctccta ctccaatatc                                    30

<210> SEQ ID NO 11
<211> LENGTH: 22
<212> TYPE: DNA
<213> ORGANISM: Artificial Sequence
<220> FEATURE:
<223> OTHER INFORMATION: Primer R303F
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (12)..(12)

```
<223> OTHER INFORMATION: k is g, or t

<400> SEQUENCE: 11
ctggaattcn nkaagggcca ga                                        22

<210> SEQ ID NO 12
<211> LENGTH: 24
<212> TYPE: DNA
<213> ORGANISM: Artificial Sequence
<220> FEATURE:
<223> OTHER INFORMATION: Primer R303R
<220> FEATURE:
<221> NAME/KEY: misc_feature
<222> LOCATION: (10)..(10)
<223> OTHER INFORMATION: m is a, or c
<220> FEATURE:
<221> NAME/KEY: misc_feature
<222> LOCATION: (11)..(12)
<223> OTHER INFORMATION: n is a, c, g, or t

<400> SEQUENCE: 12
ctggcccttm nngaattcca gacc                                      24
```